United States Patent
Markovits Rojas et al.

(10) Patent No.: US 10,196,583 B1
(45) Date of Patent: Feb. 5, 2019

(54) FISH OIL CHOLESTEROL

(71) Applicants: Alejandro Markovits Rojas, Santiago (CL); Thomas Francis Härting Glade, Santiago (CL); Steven Lee Härting Eckman, Santiago (CL)

(72) Inventors: Alejandro Markovits Rojas, Santiago (CL); Thomas Francis Härting Glade, Santiago (CL); Steven Lee Härting Eckman, Santiago (CL)

( * ) Notice: Subject to any disclaimer, the term of this patent is extended or adjusted under 35 U.S.C. 154(b) by 0 days.

(21) Appl. No.: 15/896,263

(22) Filed: Feb. 14, 2018

(51) Int. Cl.
| | |
|---|---|
| *C11B 1/10* | (2006.01) |
| *C11B 3/12* | (2006.01) |
| *B01D 3/10* | (2006.01) |
| *C07J 9/00* | (2006.01) |

(52) U.S. Cl.
CPC ............... *C11B 1/10* (2013.01); *B01D 3/10* (2013.01); *C07J 9/00* (2013.01); *C11B 3/12* (2013.01); *B01D 2257/70* (2013.01)

(58) Field of Classification Search
CPC ..... C07J 9/00; C11B 1/10; C11B 3/12; B01D 3/10; B01D 3/12
See application file for complete search history.

(56) References Cited

U.S. PATENT DOCUMENTS

| | | |
|---|---|---|
| 2,536,753 A | 1/1951 | Knol |
| 4,104,286 A | 8/1978 | Fallis et al. |
| 7,678,930 B2 * | 3/2010 | Sondbo .................... A23D 9/00 554/12 |
| 7,718,698 B2 | 5/2010 | Breivik et al. |
| 2011/0207952 A1 | 8/2011 | Avila |

FOREIGN PATENT DOCUMENTS

| | | | | |
|---|---|---|---|---|
| GB | 489 623 A | 7/1938 | | |
| GB | 526 951 A | 9/1940 | | |
| JP | S63-174997 A | 7/1988 | | |
| WO | WO-2012002210 A1 * | 1/2012 | ............... | A61K 8/06 |
| WO | 2016/096989 A1 | 6/2016 | | |
| WO | WO-2016096989 A1 * | 6/2016 | ............. | C11B 11/00 |

OTHER PUBLICATIONS

Seader et al, Separation Process Principles, 2nd edition, 2006, John Wiley & Sons, Inc., New York, pp. v.-756. (Year: 2006).*
Spiric et al., "Statistical evaluation of fatty acid profile and cholesterol content in fish (common carp) lipids obtained by different sample preparation procedures," Analytica Chimica Acta, 672:66-71 (2010).
Young, "The Chemical & Physical Properties of Crude Fish Oils for Refiners & Hydrogenators," Fish Oil Bulletin, No. 18, pp. 1-18 (1986).

* cited by examiner

*Primary Examiner* — Paul A Zucker
(74) *Attorney, Agent, or Firm* — Merchant & Gould P.C.

(57) ABSTRACT

Disclosed is a process for producing cholesterol from fish oil, including the following steps: (a) distilling fish oil in a vacuum distillation column to obtain a first residue and a first distillate, (b) distilling the first distillate in a vacuum distillation column to obtain a second distillate and a second residue, (c) contacting the second residue with an alkali to produce a saponified mixture, (d) contacting the saponified mixture with a non-polar organic solvent or a mixture of non-polar organic solvents to produce an organic phase and an aqueous phase, (e) separating the organic phase from the aqueous phase, (f) cooling the organic phase to form a solid phase and a liquid phase, and (g) separating the solid phase from the organic phase, wherein the separated solid phase includes cholesterol.

13 Claims, No Drawings

FISH OIL CHOLESTEROL

FIELD OF THE INVENTION

The present invention is related to a process for the production of cholesterol from fish oil.

BACKGROUND

Currently there is a growing demand for cholesterol of pharmaceutical grade having a cholesterol content of 95% or more for the production of vitamins D2, D3, hormones and W/O emulsions in cosmetics.

Currently cholesterol at industrial scale is mainly produced from wool wax alcohols, i.e. the non-saponifiable fraction of wool grease, which contains from about 25% to about 32% of cholesterol. Most common processes for producing cholesterol comprise the formation of an insoluble addition product by reacting cholesterol with a metal salt followed by the decomposition of the adduct and the recovery of cholesterol. Such processes are able to meet the requirements of purity for pharmaceutical applications of cholesterol. For example, U.S. Pat. No. 2,536,753 discloses a process, wherein the metal salt is zinc chloride.

However, this known process generates large amounts of liquid industrial waste (LIW), the management of which can significantly increase production costs. In addition worldwide demand for wool has declined steeply over the past decades, which has led to far smaller sheep stocks and lower availability of wool grease, making it necessary to look at additional sources of supply of cholesterol.

Spiric A. et al: "Statistical evaluation of fatty acid profile and cholesterol content in fish (common carp) lipids obtained by different sample preparation procedures" Analytical Chimica Acta, vol. 672, no. 1-2 Jul. 2010, pp. 67-71 discloses a process for extracting cholesterol from fish tissues by saponification at 80° C. followed by extraction with hexane and diethyl ether.

GB 526951 discloses a process for the extraction of cholesterol from animal tissues such as brain, spinal cord, etc. by saponification and extraction with a non-water miscible solvent.

GB 489623 discloses a process for obtaining cholesterol from marine animal oils by subjecting the oil to fractionation by multiple sequential vacuum distillations of the oil at different temperatures and pressures, wherein one of the distillate fraction comprise cholesterol, both free and esterified. Such fraction comprising cholesterol, if desired, may be further purified by saponification of the fraction followed by extraction of non-saponifiable matter, concentration and crystallization.

In Example 1 of GB 489623, clarified whale oil is subjected to molecular distillation at a temperature of 90° C. to 220° C. and pressure of 0.001 to 0.003 mmHg. As the pressure is lowered and the temperature is raised, successive fractions amounting to 0.2 to 2% are withdrawn, such fractions comprising most of the free fatty acids, squalene and other volatiles. More fractions in proportions ranging from 0.5 to 10% are withdrawn between about 120° C. and 160° C., such fractions comprising free and esterified cholesterol. It is evident that that no less than four consecutive distillations, each at some specific temperature and pressure, are required to arrive at a cholesterol rich fraction using this process.

There are several other disadvantages of the process disclosed by GB 489623 as well. At present, fish oil is a valuable commodity due to its content of eicosapentaenoic (EPA) and docosahexaenoic (DHA) acid. Multiple distillations of fish oil increase the trans fatty acid content of the oil, and promote polymerization of unsaturated fatty acid, which in turn decreases the content of EPA and DHA. Multiple distillations thus render the fish oil unsuitable for human or animal consumption.

On the other hand, present day fish oils contain a great variety of toxic and/or harmful anthropogenic contaminants like polychlorinated biphenyls (PCB), dichlorodiphenyl-trichloroethane (DDT) and its metabolites, dibenzo-dioxins (PCDDs), and dibenzo-furans (PCDFs), poly-aromatic hydrocarbons (PAH), pesticides and their degradation products, also known as persistent organic pollutants or POP's, which are resistant to environmental degradation and thus bio-accumulate. Therefore, the distillate fractions comprising cholesterol will comprise as well one or more of such contaminants. The content of such contaminants in the distillate fractions will be even higher than in the fish oil. This fact, though evident, can be found in the prior art.

U.S. Pat. No. 7,678,930 discloses a process for obtaining a free cholesterol-reduced fish oil by vacuum stripping the oil. On the other hand, U.S. Pat. No. 7,718,698 discloses a process for decreasing the amount of environmental pollutants in fish oil, also by vacuum stripping the oil. These two patents have similar disclosures. Therefore, under conditions of vacuum distillation where environmental pollutants are removed, free cholesterol is removed as well and vice versa.

The distillate of the process of U.S. Pat. No. 7,678,930 has a level of toxic and/or harmful anthropogenic contaminants higher than the fish oil and its cholesterol content is no greater than 10%, therefore it is unsuitable as a source of cholesterol in formulated shrimp and prawn feed. The same can be said of the cholesterol concentrates obtained by the process disclosed in GB 489623. Because cholesterol is obtained from such concentrates in GB 489623 by methods such as saponification followed by extraction of the non-saponifiable matter (which comprises all the POPs as well) with a water immiscible solvent, concentration and crystallization, the crystallized solid cholesterol will also contain contaminants, which by itself is sufficient to preclude its use for pharmaceutical purposes.

U.S. Pat. No. 4,104,286 discloses a process for isolating cholesterol from dried whole egg.

US 2011/0207952 discloses a process of cholesterol extraction from an algal processing waste discloses a process of saponifying a fat or oil, extracting with solvent the saponified mixture and extracting cholesterol from the solution stream.

JPS 63174997 with supercritical carbon dioxide.

International Application WO2016/096989 discloses a method for extracting cholesterol from a fish oil waste residue, the residue of a standard process for the production of concentrates of EPA and DHA from fish oil, containing up to 15% of cholesterol. It is known to a skilled person that such residue corresponds to about 1% of the original fish oil, which is equivalent to less than 10% of cholesterol present in original fish oil.

SUMMARY OF THE INVENTION

In one aspect, the disclosed technology relates to a process for producing cholesterol from fish oil, comprising the following steps: (a) distilling fish oil in a vacuum distillation column to obtain a first residue and a first distillate, (b) distilling the first distillate in a vacuum distillation column to obtain a second distillate and a second residue, (c) contacting the second residue with an alkali to produce a saponified mixture, (d) contacting the saponified mixture with a non-polar organic solvent or a mixture of non-polar organic solvents to produce an organic phase and an aqueous phase, (e) separating the organic phase from the aqueous phase, (f) cooling the organic phase to form a solid phase and a liquid phase, and (g) separating the solid phase from the organic phase, wherein the separated solid phase comprises cholesterol.

In one embodiment, in step (a) the fish oil is distilled in an admixture with an auxiliary fluid. In another embodiment, the vacuum distillation column is a short-path distillation column. In another embodiment, the fish oil is fed into the vacuum distillation column in step (a) at a rate of 1 to 150 kg/h per $m^2$ of evaporator area. In another embodiment, the weight ratio of the auxiliary fluid to the fish oil in the mixture is about 1:100 to 10:100. In another embodiment, the admixture is fed into the vacuum distillation column at a rate of 1 to 150 kg/h per $m^2$ of evaporator area. In another embodiment, step (a) is conducted at an evaporation temperature of 150 to 300° C. and a column pressure of 0.0001 to 0.5 mbar. In another embodiment, the first distillate is fed into the vacuum distillation column in step (b) at a rate of 10 to 350 kg/h per $m^2$ of evaporator area. In another embodiment, step (b) is conducted at an evaporation temperature of 100 to 250° C. and a column pressure of 0.0001 to 0.5 mbar. In another embodiment, the alkali of step (c) is NaOH or KOH. In another embodiment, the non-polar organic solvent or the mixture of non-polar organic solvents of step (d) comprises aliphatic hydrocarbon solvent. In another embodiment, the organic phase and the aqueous phase are separated by decanting or centrifuging. In another embodiment, the separated organic phase is kept at less than 30° C. to form a solid phase and a liquid phase. In another embodiment, in step (g) the separated solid phase comprises at least 95% of cholesterol.

An objective of the present invention is to provide a process for obtaining from fish oil with a yield of at least 50% on the basis of fish oil, a pharmaceutical grade cholesterol having at least 95% of cholesterol and a level of toxic and/or harmful anthropogenic contaminants (POPs) lower than in the fish oil, and simultaneously producing a residual or processed fish oil of high-quality suitable for animal or human consumption or for the elaboration of EPA and DHA concentrates.

The product of the present invention in addition to its use in processes for the production of vitamins D2, D3, hormones and water-in-oil (W/O) emulsions in cosmetics, can be utilized as well as a feed ingredient in formulated feed for shrimp and prawn.

One or more objectives of the invention are achieved by the following process:

a) distilling fish oil in a vacuum distillation column to obtain a first residue and a first distillate,
b) distilling the first distillate in a vacuum distillation column to obtain a second distillate and a second residue,
c) contacting the second residue with an alkali to produce a saponified mixture,
d) contacting the saponified mixture with an organic solvent immiscible with water or mixture of organic solvents immiscible with water to produce an organic and aqueous phase,
e) separating the organic phase from the aqueous phase,
f) cooling the organic phase to form a solid phase and a liquid phase and
g) separating the solid phase from the organic phase Fish Oil.

As used herein, the term "fish oil" refers to oils obtained from wild and farmed fish, crustaceans and other marine animals. Such oils are obtained from the whole body of the fish or from its by-products such as liver, head etc. Examples of such oils comprise anchovy oil, sardine oil, salmon oil, jack mackerel oil, menhaden oil, tuna oil, krill oil, squid oil, pollock oil, herring oil, capelin oil, cod liver oil and squid oil. Fish oils may be derived from a single species or mixtures of fish oils.

Fish oil also refers to any fish oil from fish oil/meal factories, including degummed or bleached fish oil or neutralized fish oil. Such oils, in addition to triglycerides, their main component, typically comprise between 0.01 to 10% of free fatty acids and about 2% or less of non-saponifiable matter composed primarily of cholesterol, glyceryl ethers, fatty alcohols, squalene and saturated hydrocarbons. (Young, F. V. K. "The Chemical & Physical Properties of Crude Fish Oils for Refiners & Hydrogenators" Fish Oil Bulletin No. 18, 1986). The average cholesterol content of fish oil is about 1%.

In the present invention a vacuum distillation column may be a short-path distillation column having an internal condenser at the proximity of the heated surface or evaporator. The short-path distillation column is also known as a molecular distillation column when the distance between the evaporator and the condenser is comparable to the mean free path of the distillate molecules under the operating conditions. Therefore, in the present invention vacuum distillation column may be a short-path distillation column, a molecular distillation column, or an equivalent thereof.

a) Distilling the Fish Oil

The fish oil is fed into a vacuum distillation column, generally at a rate in the range of 1 to 150 kg/h per $m^2$ of evaporator area, preferably at a rate in the range 10 to 100 kg/h per $m^2$ of evaporator area.

In an embodiment, the evaporation temperature is between 150° C. and 300° C., preferably between 180° C. and 280° C. In an embodiment, the column pressure is between 0.0001 mbar and 0.5 mbar, preferably between 0.001 and 0.1 mbar. In an embodiment, the evaporation temperature is between 150° C. and 300° C., preferably between 180° C. and 280° C., and the column pressure is between 0.0001 mbar and 0.5 mbar, preferably between 0.001 and 0.1 mbar.

The distillation process results in the separation of a first distillate comprising cholesterol, other non-saponifiable matter of the fish oil, free fatty acids and anthropogenic contaminants, and a first residue comprising fish oil with decreased content of cholesterol, non-saponifiable matter and anthropogenic contaminants. The first distillate condenses at the internal condenser. The first distillate and the first residue leave the column separately and are collected at the column exit. The first residue is a high quality fish oil suitable for human or animal consumption or for the elaboration of EPA and DHA concentrates.

In case the free fatty acid content of the fish oil is less than about 6%, which always occurs in neutralized fish oil, the first distillate rich in cholesterol, at the temperature of the condenser which is preferably lower than 60° C., may form a very viscous slow flowing film at the condenser or may even solidify, thus clogging the condenser. This is due to the high melting point of the cholesterol (136° C.). There are two solutions provided to this problem in the state of art, both resorting to some auxiliary fluid (AF). In one solution, the AF is contacted with the fish oil to form an admixture and the admixture is distilled at the conditions of temperature and pressure as described above. The second solution consists in feeding the AF directly over the condenser surface.

An auxiliary fluid (AF) when utilized in an admixture with fish oil, includes any fluid or mixture of fluids which distills at the vacuum distilling conditions disclosed above, and is also in a liquid state at the condenser temperature and dissolves or is miscible with cholesterol, thus reducing its concentration in the condensed film, therefore forming a free downward flowing fluid mixture at the condenser, and preventing clogging or fouling of the condenser. Any fluid or fluid mixture fulfilling the above requirements can be used as an auxiliary fluid, though preferred auxiliary fluids for the present invention include ethyl esters of unsaturated fatty acids or mixtures of ethyl esters of fatty acids mostly composed of unsaturated fatty acids, because such auxiliary fluids allow the use of lower condenser temperature which in turn improves the vacuum system performance and reduces the re-evaporation rate of the condensates, thereby improving the overall removal yield of the desired distillate.

If the AF is utilized in an admixture with the fish oil, the proportion of auxiliary fluid relative to the fish oil in the admixture is about 1 to 10%, preferably from about 2 to 8%. The admixture, in auxiliary fluid free basis, is fed into the vacuum distillation column, at the rate described above and distilling conditions are the same as described above without auxiliary fluid, but the first distillate additionally comprises the auxiliary fluid as well.

b) Distilling the First Distillate.

The first distillate is fed into a vacuum distillation column at a rate from 10 to 350 kg/h per $m^2$ of evaporating surface, preferably from 50 to 200 kg/h per $m^2$.

In an embodiment, the evaporation temperature is between 100° C. and 250° C., preferably between 140° C. and 220° C. In an embodiment, the column pressure is between 0.0001 mbar and 0.5 mbar, preferably between 0.001 and 0.1 mbar. In an embodiment, the evaporation temperature is between 100° C. and 250° C., preferably between 140° C. and 220° C., and the column pressure is between 0.0001 mbar and 0.5 mbar, preferably between 0.001 and 0.1 mbar.

The distillation process of the first distillate results in the production of a second distillate which condenses at the internal condenser, and a second residue comprising cholesterol.

The second distillate and the second residue leave the vacuum distillation column separately and are collected at the column exit.

c) Saponifying the Second Residue.

Next, the second residue is saponified. To this end, the second residue is contacted with an alkali such as NaOH or KOH in water to form a saponifying mixture. The weight ratio of the second residue to the water is from 1:0.1 to 1:10, preferably from 1:0.1 to 1:1. Alternatively, the second residue is contacted with an alkali such as NaOH or KOH in a solution comprising water and a polar solvent such as methanol or ethanol or any mixture of said solvents to form a saponifying mixture. The weight ratio of the second residue to the solution is from 1:0.1 to 1:10, preferably from 1:0.1 to 1:1

The amount of alkali in the water or solution is equal to the saponification value of the second residue, preferably from 1.01 to 1.20 times the saponification value of the second residue.

The saponifying mixture is fed to a closed vessel and heated at a temperature in the range of 30 to 150° C. from 5 to 120 minutes, preferably from 10 to 30 minutes, to form a saponified mixture.

Next, the saponified mixture is contacted with one or more non-polar organic solvents, such as an aliphatic hydrocarbon such as hexane, heptane, octane, petroleum ether, cyclohexane, cycloheptane, benzene or toluene, resulting in the separation of two immiscible phases, an organic phase comprising cholesterol and an aqueous phase comprising fatty acid soaps. The weight ratio of the saponified mixture to the organic solvent is from 1:0.5 to 1:10, preferably from 1:1 to 1:5.

In case the saponification of the second residue was made with NaOH or KOH in water alone, in order to facilitate phase separation, one or more polar solvents such as water, ethanol, methanol or acetone can be added to the saponified mixture contacted with one or more non-polar organic solvents, such as an aliphatic hydrocarbon, benzene or toluene.

The contacting of the saponified mixture with the solvent or solvents is carried out in a closed agitated vessel at a temperature of 10 to 180° C., preferably 20 to 120° C. during a time interval of 1 to 60 minutes, preferably of 2 to 15 minutes, after which the organic and aqueous phases are separated from each other either by, e.g., settling or centrifuging. If needed, the separated aqueous phase can be contacted with one or more non-polar solvents to form two additional immiscible phases.

The solid concentration in separated organic phase can be increased by partially evaporating solvent until a solid content of 1 to 40%, preferably 5 to 30%, is reached. The concentrated organic phase is kept at a temperature of less than 30° C., preferably less than 20° C., until a solid-liquid mixture is formed. The solids are separated from the mixture by, e.g., filtration or centrifugation. The separated solid having a level of anthropogenic contaminants lower than the fish oil is comprised at least 95% of cholesterol.

A better understanding of the present invention may be obtained in light of the following examples which are set forth to illustrate, but are not to be construed to limit the present invention.

COMPARATIVE EXAMPLE

Cholesterol from Anchovy Oil According to the Process of Patent GB 489623.

Anchovy oil was processed according to the process disclosed in patent GB 489623, as embodied in Example 1 of GB 489623 for whale oil.

100 kg of the anchovy oil having a total cholesterol content of 7.4 mg/g was fed to a VK 83 short path distillation column and distilled at the temperature of 90° C. and the pressure of 0.003 mbar. The condenser temperature was set at 50° C. A distillate D1 in the amount of 1.6 kg was obtained together with a residue R1, the residual anchovy oil of the first distillation. The content of cholesterol of D1 was below 0.1%.

Next, R1 was fed to a VK 83 short path distillation column and distilled at the temperature of 130° C. and the pressure of 0.002 mbar. The condenser temperature was set at 50° C. A distillate D2 in the amount of 1.1 kg was obtained together with a residue R2, the residual anchovy oil of the second distillation. The content of cholesterol of D2 was 0.8%.

As the D2 split was low, around 1%, the following distillations were done using an auxiliary fluid of the composition shown in Table 1 below. It should be noted, that in similar circumstances, use of an auxiliary fluid may help prevent the clogging of the condenser, as disclosed in U.S. Pat. No. 2,126,467.

R2 was admixed with 5 kg of auxiliary fluid of the composition shown in Table 1 and the mixture was fed to a VK 83 short path distillation column and distilled at the temperature of 180° C. and the pressure of 0.002 mbar. The condenser temperature was set to 20° C. A distillate D3 in the amount of 5.8 kg was obtained together with a residue R3, the residual anchovy oil of the third distillation. The content of cholesterol in D3 was 6.6%.

Next, R3 was admixed with 5 kg of auxiliary fluid of the composition shown in Table 1 and the mixture was fed to a VK 83 short path distillation column and distilled at the temperature of 220° C. and the pressure of 0.002 mbar. The condenser temperature was set to 20° C. A distillate D4 in the amount of 5.3 kg was obtained together with a residue R4, the residual anchovy oil of the fourth distillation. The content of cholesterol in D3 was 6.2%.

TABLE 1

Auxiliary fluid composition in Comparative Example.

| Fatty acid ethyl ester | Composition concentration, % |
|---|---|
| Myristic acid (C14:0) ethyl ester. | 6.6 |
| Palmitic acid (C16:0) ethyl ester | 8.2 |
| Palmitoleic acid (C16:1) ethyl ester | 46.4 |
| Stearic acid (C18:0) ethyl ester | 1.9 |
| Oleic acid (C18:1) ethyl ester | 29.3 |
| Linoleic acid (C18:2) ethyl ester | 4.1 |
| Alpha-linolenic acid (18:3) ethyl ester | 3.5 |

Next, 580 g of D3 and 530 g of D4 were combined and saponified. Extraction was performed two times with 5 kg of ethyl ether. The ethyl ether extract was evaporated recovering 94 g of residue. The residue was dissolved with 250 g of ethyl acetate and cooled in a refrigerator overnight. Solid crystals were formed. The solids were separated by filtration and then dried in a vacuum oven to obtain 62 g of dry solids having a cholesterol concentration of 90.4%. Total poly aromatic hydrocarbons (PAH) of the solids was 31.5 ppb, higher than in the original anchovy oil.

Concerning the residual fish oil of each distillation, Table 2 shows the combined EPA and DHA content, trans fatty acid content and acid number of each residue.

TABLE 2

Combined EPA and DHA content, trans fatty acid content an acid number

| | Anchovy Oil | R1 | R2 | R3 | R4 |
|---|---|---|---|---|---|
| EPA + DHA, % | 26.7 | 26.8 | 26.2 | 25.1 | 24.3 |
| Trans Fatty Acids, % | 0.3% | 0.3% | 0.4% | 0.6% | 0.7% |
| Acid Number, mg KOH/g | 6.3 | 0.3 | 0.1 | <0.05 | <0.05 |

As can be observed in Table 2, the obtaining of cholesterol fractions by fractionation of the fish oil as disclosed in patent GB 489623, leads to an increase of the trans fatty content and a loss of (EPA+DHA), presumably due to polymerization in the residual fish oil. After four successive distillations, the trans fatty acid content increased by about 130% and the EPA+DHA content decreased by about 9%.

Comparative Example shows that cholesterol obtained according to the process of GB 489623 is not a pharmaceutical grade cholesterol, contains a detectable amount of impurities coming from fish oil, and thus the residual or processed fish oil is not suitable for human or animal consumption.

EXAMPLE 1

Cholesterol from Neutralized Anchovy Oil.

Anchovy oil (same raw material as in Example 1) was neutralized with caustic soda and washed with hot water to yield a neutralized anchovy oil with an acid number of 0.2 mg KOH/g.

250 kg of the neutralized anchovy oil was admixed with 15 kg of the auxiliary fluid set forth in Table 1.

The admixture was fed to a VK 83 short path distillation column and distilled at the temperature of 253° C. and the pressure of 0.008 mbar. The condenser temperature was set at 20° C. A distillate D1 in the amount of 18 kg was obtained together with a residue of anchovy oil R1.

Next, 15 kg of distillate D1 was fed to a VK 83 short path distillation column at the temperature of 155° C. and the pressure of 0.007 mbar. The condenser temperature was set at 20° C. A residue R2 in the amount of 3.5 kg was obtained.

Next, 1 kg of R2 was contacted in a stirred reactor with 2 kg of water, 1 kg of ethanol (190 proof) and 110 g of NaOH (99%) to form a first mixture, stirred and heated to 77° C. for a period of time of 2 hours. Then the mixture was cooled to 35° C. and contacted in the same reactor with 5 kg of hexane to form a second mixture which was stirred for 5 minutes then let to stand until two immiscible phases were formed: a first aqueous phase and a first organic phase. After separating the two phases, the first aqueous phase was contacted with 5 kg of fresh hexane to form a second mixture which was agitated for 5 minutes and then let to settle to form a second organic phase and a second aqueous phase. After separating these phases, the first and second organic phases were combined and the combination was contacted with 500 g of water and 500 g of ethanol, agitated and then let to stand until a third organic phase and a third aqueous phase was formed. The third organic phase was separated from the third aqueous phase and then partially evaporated to obtain 1752 g of a residue R3.

Next, residue R3 was cooled overnight in a refrigerator at 5° C. Solid crystals were formed. The solids were separated by filtration and then dried in a vacuum oven to obtain 261 g of dry solids.

Table 3 below presents the analytical results for the Example 1.

TABLE 3

Analytical results for the Example 1.

| | Neutralized Anchovy oil | Distillate D1 | Dry Solid |
|---|---|---|---|
| Free cholesterol, mg/g | 7.0 | 92.7 | 971.5 |
| Total cholesterol, mg/g | 7.4 | 93.0 | 971.5 |
| Cholesterol ester[1], mg/g | 0.8 | 0.5 | <LOQ |
| Non-saponifiable matter, % | 1.38 | 13.40 | 100 |
| Acid number, mg KOH/g | 0.2 | 2.6 | <LOQ |
| Dioxins, Furans and Dioxin like PCBs, TEQ ppt (lower bound) | 1.41 | 12.83 | <LOQ |
| PCB 209, ppb (lower bound) | 18.53 | 225.27 | <LOQ |
| Total PAHs, ppb | 14.11 | 133.6 | <LOQ |
| Pesticides, ppb | 18.4 | 241.3 | <LOQ |

[1]As mg of cholesteryl oleate/g of sample.
LOQ: Limit of Quantification

In R1, there was no difference between the trans fatty acid and EPA+DHA content with respect to the anchovy oil, and the concentrations of toxic and/or harmful anthropogenic contaminants were below the quantification limits.

EXAMPLE 2

Cholesterol from Sardine Oil 240 kg of sardine oil was fed to a VK 83 short path distillation column and distilled at the temperature of 253° C. and the pressure of 0.03 mbar. The condenser temperature was set to 50° C. A distillate D1 in the amount of 18.6 kg together with a residue of sardine oil R1 was obtained.

Next, 10 kg of distillate D1 was fed to a VK 83 short path distillation column at the temperature of 170° C. and the pressure of 0.01 mbar. The condenser temperature was set to 40° C. A residue R2 in the amount of 3.3 kg was obtained.

Next, 1 kg of R2 was contacted in a stirred reactor with 1.5 kg of water, 1 kg of ethanol (190 proof) and 105 g of NaOH (99%) to form a first mixture, stirred and heated to 78° C. for a period of time of 2 hours. Then the mixture was cooled to 35° C. and contacted in the same reactor with 5 kg of petroleum ether to form a second mixture which was stirred for 5 minutes then let to stand until two immiscible phases were formed: a first aqueous phase and a first organic phase. After separating the two phases, the first aqueous phase was contacted with 5 kg of fresh hexane to form a second mixture which was agitated for 5 minutes and then let to settle to form a second organic phase and a second aqueous phase. After separating these phases, the first and second organic phases were combined and the combination was contacted with 500 g of water and 500 g of ethanol, agitated and then let to stand until a third organic and a third aqueous phase was formed. The third organic phase was separated from the third aqueous phase and then partially evaporated to obtain 1600 g of a residue R3.

Next, R3 was contacted with 200 g of ethanol (190 proof) and cooled in a refrigerator at 5° C. for 8 hours. Solid crystals were formed. The solids were separated by filtration and then dried in a vacuum oven to obtain 252 g of dry solids.

Table 4 below presents the analytical results for the Example 2.

TABLE 4

Analytical results for Example 2.

| | Sardine oil | Distillate D1 | Dry Solid |
|---|---|---|---|
| Free cholesterol, mg/g | 9.3 | 118.6 | 964.9 |
| Total cholesterol, mg/g | 9.6 | 118.9 | 964.9 |
| Cholesterol ester[1], mg/g | 0.5 | 0.5 | <LOQ |
| Unsaponifiable matter, % | 1.47 | 16.01 | 100 |
| Acid number, mg KOH/g | 14.4 | 171.3 | <LOQ |
| Free (EPA + DHA) % | 0.5 | 6.8 | <LOQ |
| Dioxins, Furans and Dioxin like PCBs, TEQ ppt (lower bound) | 1.61 | 16.96 | <LOQ |
| PCB 209, ppb (lower bound) | 17.21 | 218.12 | <LOQ |
| Total PAHs, ppb | 28.15 | 328.63 | <LOQ |
| Pesticides, ppb | 21.0 | 248.5 | <LOQ |
| Inorganic As, ppm | 2.2 | <LOQ | <LOQ |
| Heavy metals, ppm | 0.06 | <LOQ | <LOQ |

[1]As mg of cholesteryl oleate/g of sample.
LOQ: Limit of Quantification

In R1, there was no difference between the trans fatty acid and EPA+DHA content with respect to the anchovy oil, and the concentrations of toxic and/or harmful anthropogenic contaminants were below the quantification limits.

EXAMPLE 3

Cholesterol from Bleached Sardine Oil 250 kg of sardine oil with 2 kg of bleaching clay was heated at 70° C. and at a vacuum of 50 mbar in a stirred vessel for 30 minutes. After separating the clay by filtration, 245 kg of bleached sardine oil was obtained.

240 kg of bleached sardine oil was admixed with 10 kg of auxiliary fluid of the composition shown in Table 2 above and the admixture was fed to a VK 83 short path distillation column and distilled at the temperature of 245° C. and the pressure of 0.008 mbar. The condenser temperature was set to 20° C. A distillate D1 in the amount of 21.3 kg and a residue bleached sardine oil R1 were obtained.

Next, 15 kg of distillate D1 was fed to a VK 83 short path distillation column at the temperature of 167° C. and the pressure of 0.004 mbar. The condenser temperature was set to 20° C. A residue R2 in the amount of 4.4 kg was obtained.

Next, 1 kg of R2 was contacted in a stirred reactor with 2 kg of water, 2 kg of ethanol (190 proof) and 130 g of NaOH (99%) to form a first mixture, stirred and heated to 78° C. for a period of time of 1 hour. Then the mixture was cooled to 40° C. and contacted in the same reactor with 5 kg of cyclohexane to form a second mixture which was stirred for 5 minutes then let to stand until two immiscible phases were formed: a first aqueous phase and a first organic phase. After separating the two phases, the first aqueous phase was contacted with 5 kg of fresh cyclohexane to form a second mixture which was agitated for 5 minutes and then let to settle to form a second organic phase and a second aqueous phase. After separating these phases, the first and second organic phases were combined and the combination was contacted with 500 g of water and 500 g of ethanol, agitated and then let to stand until a third organic phase and a third aqueous phase was formed. The third organic phase was separated from the third aqueous phase, and then evaporated to dryness to obtain 251 g of a residue R3.

Next, the residue R3 was dissolved with 1.2 kg of acetone at 55° C. cooled in a refrigerator at 5° C. for 24 hours. Solid crystals were formed. The solids were separated by filtration and then dried in a vacuum oven to obtain 189 g of dry solids. Table 5 presents the analytical results for Example 3.

TABLE 5

Analytical results for Example 3

| | Sardine oil | Distillate D1 | Dry Solid |
|---|---|---|---|
| Free cholesterol, mg/g | 7.5 | 82.5 | 975.1 |
| Total cholesterol, mg/g | 8.2 | 83.9 | 975.1 |
| Cholesterol ester[1], mg/g | 1.2 | 2.4 | <LOQ |
| Unsaponifiable matter, % | 1.66 | 13.04 | 100 |
| Acid number, mg KOH/g | 7.3 | 171.0 | <LOQ |
| Free (EPA + DHA) % | 0.7 | 7.6 | <LOQ |
| Dioxins, Furans and Dioxin like PCBs, TEQ ppt(lower bound) | 3.61 | 17.08 | <LOQ |
| PCB 209, ppb(lower bound) | 17.45 | 247.49 | <LOQ |
| Total PAHs, ppb | 22.1 | 256.4 | <LOQ |
| Pesticides, ppb | 12.9 | 142.7 | <LOQ |
| Inorganic As, ppm | 5.2 | <LOQ | <LOQ |
| Heavy metals, ppm | 0.04 | <LOQ | <LOQ |

[1]As mg of cholesteryl oleate/g of sample.
LOQ: Limit of Quantification

In R1, there was no difference between the trans fatty acid and EPA+DHA content with respect to the anchovy oil, and the concentrations of toxic and/or harmful anthropogenic contaminants were below the quantification limits.

EXAMPLE 4

Contaminant Analysis of the Dry Solids from Example 2

A comprehensive contaminant analysis was performed on the cholesterol product of Example 2. The results are shown in Table 6:

TABLE 6

| | | Dried solids of Example 2 |
|---|---|---|
| Dioxins and Furans (17 PCDD/F) | WHO(2005)-PCDD/F TEQ (lower-bound), pg/g | <LOQ |
| Polychlorinated biphenyls (12 WHO PCB) | WHO(2005)-PCB TEQ (lower-bound), pg/g | <LOQ |
| Polychlorinated biphenyls (6 ICES PCB) | Total 6 ndl-PCB (lower-bound), ng/g | <LOQ |
| TEQ-Totals WHO-PCDD/F and PCB | WHO(2005)-PCDD/F + PCB TEQ (lower-bound), pg/g | <LOQ |
| PCB 209, polychlorinated biphenyls 209 in total | Total Mono- to DecaCB (lower bound), ng/g | <LOQ |
| Polybrominated biphenyls ethers (24 PBDE) | sum of 24 BDEs (excl. LOQ), ng/g | <LOQ |
| Ester-bound 2-chloropropane-1,3-diol (2-MCPD ester) | Total 2-MCPD (free and bound), µg/kg | <LOQ |
| Ester-bound 3-chloropropane-1,2-diol (3-MCPD ester) | Total 3-MCPD (free and bound), µg/kg | <LOQ |
| Ester-bound 3-chloropropane-1,2-diol (3-MCPD ester) and glycidol (glycidyl ester) | Total 3-MCPD (free and bound), µg/kg | <LOQ |
| Arsenic (As) | Arsenic (As), mg/kg | <LOQ |
| 13 PAH (EPA)[1] | Sum of all positive identified PAH, µg/kg | <LOQ |
| Benzo(a)pyrene | Benzo(a)pyrene, µg/kg | <LOQ |
| Organochlorine Pesticides and Pyrethroides | DDT (total), mg/kg | <LOQ |
| Organochlorine Pesticides and Pyrethroides | DDE, p,p'-, mg/kg | <LOQ |
| Methoxylated (MeO-) PBDEs | 2-MeO-PBDE-68, ng/g | <LOQ |
| Methoxylated (MeO-) PBDEs | 2-MeO-PBDE-47, ng/g | <LOQ |

[1]Environmental Protection Agency
LOQ: Limit of Quantification

2-MeO-PBDE-68 and 2-MeO-PBDE-47 are naturally occurring methoxylated PBDEs which accumulate in fish oil via the marine food web but may also originate by biotransformation of PBDEs.

Examples show that cholesterol obtained according to the present invention is a pharmaceutical grade cholesterol, does not contain a detectable amount of impurities coming from fish oil, and thus the residual or processed fish is suitable for human or animal consumption.

All references cited and/or discussed in this specification are incorporated herein by reference in their entireties and to the same extent as if each reference was individually incorporated by reference.

The invention claimed is:

1. A process for producing cholesterol from fish oil, comprising the following steps:
   (a) distilling fish oil in a vacuum distillation column to obtain a first residue and a first distillate, wherein the fish oil is distilled in an admixture with an auxiliary fluid comprising an ethyl ester of a fatty acid,
   (b) distilling the first distillate in a vacuum distillation column to obtain a second distillate and a second residue,
   (c) contacting the second residue with an alkali metal hydroxide to produce a saponified mixture,
   (d) contacting the saponified mixture with a non-polar organic solvent or a mixture of non-polar organic solvents to produce an organic phase and an aqueous phase,
   (e) separating the organic phase from the aqueous phase,
   (f) cooling the organic phase to form a solid phase and a liquid phase, and
   (g) separating the solid phase from the organic phase, wherein the separated solid phase comprises cholesterol comprising at least 95 wt. % of cholesterol and having a lower content of anthropogenic contaminants than the fish oil, wherein the cholesterol is formed in a single extraction-crystallization step.

2. The process according to claim 1, wherein the vacuum distillation column is a short-path distillation column.

3. The process according to claim 1, wherein the fish oil is fed into the vacuum distillation column in step (a) at a rate of 1 to 150 kg/h per m² of evaporator area.

4. The process according to claim 1, wherein the weight ratio of the auxiliary fluid to the fish oil in the mixture is about 1:100 to 10:100.

5. The process according to claim 1, wherein the admixture is fed into the vacuum distillation column at a rate of 1 to 150 kg/h per m² of evaporator area.

6. The process according to claim 1, wherein step (a) is conducted at an evaporation temperature of 150 to 300° C. and a column pressure of 0.0001 to 0.5 mbar.

7. The process according to claim 1, wherein the first distillate is fed into the vacuum distillation column in step (b) at a rate of 10 to 350 kg/h per m² of evaporator area.

8. The process according to claim 1, wherein step (b) is conducted at an evaporation temperature of 100 to 250° C. and a column pressure of 0.0001 to 0.5 mbar.

9. The process according to claim 1, wherein the alkali metal hydroxide of step (c) is NaOH or KOH.

10. The process according to claim 1, wherein the non-polar organic solvent or the mixture of non-polar organic solvents of step (d) comprises aliphatic hydrocarbon solvent.

11. The process according to claim 1, wherein the organic phase and the aqueous phase are separated by decanting or centrifuging.

12. The process according to claim 1, wherein the separated organic phase is kept at less than 30° C. to form a solid phase and a liquid phase.

13. The process according to claim 1, wherein the ethyl ester of a fatty acid are C10 to C22 fatty acids.

* * * * *